United States Patent [19]

Arnold et al.

[11] Patent Number: 5,893,714
[45] Date of Patent: Apr. 13, 1999

[54] CARTRIDGE FOR CONTAINING MATERIAL IN PASTE FORM

[75] Inventors: Helmut Arnold, Frankfurt am Main; Markus Balkenhol, Bechum; Dieter Schödel, Wiesbaden, all of Germany

[73] Assignee: Heraeus Kulzer GmbH, Hanau, Germany

[21] Appl. No.: 08/967,701

[22] Filed: Nov. 10, 1997

[30] Foreign Application Priority Data

Dec. 10, 1996 [DE] Germany .................. 196 51 139

[51] Int. Cl.⁶ .................................................. A61C 5/04
[52] U.S. Cl. ............................................................ 433/90
[58] Field of Search .................. 433/89, 90; 604/189, 604/235

[56] References Cited

U.S. PATENT DOCUMENTS

| | | | |
|---|---|---|---|
| 3,436,828 | 4/1969 | Dragan | 433/90 |
| 4,391,590 | 7/1983 | Dougherty | 433/90 |
| 4,457,712 | 7/1984 | Dragan | 433/90 |
| 4,819,836 | 4/1989 | Meckenstock | 222/386 |
| 5,056,690 | 10/1991 | Ichihara et al. | 222/386 |
| 5,061,179 | 10/1991 | Dragan | 433/90 |
| 5,122,057 | 6/1992 | Discko, Jr. | 433/90 |
| 5,267,859 | 12/1993 | Discko, Jr. | 433/89 |
| 5,514,113 | 5/1996 | Anderson et al. | 433/90 |
| 5,531,709 | 7/1996 | Eykmann et al. | 433/90 |

FOREIGN PATENT DOCUMENTS

| | | |
|---|---|---|
| 1323631 | 7/1963 | France . |
| 30 26 659 | 2/1982 | Germany . |
| 3031939 | 4/1982 | Germany . |
| 2 142 245 | 1/1985 | United Kingdom . |

*Primary Examiner*—Cary E. O'Connor
*Attorney, Agent, or Firm*—Sprung Kramer Schaefer & Briscoe

[57] ABSTRACT

A cartridge for containing material in paste form, having a cylindrical container unit, an outlet tip with an outlet passage disposed at one end of the container unit at an angle to its axis, a protective cap encasing the outlet tip, a mounting disposed at the second end of the cylindrical container unit, which is provided for mounting the cartridge in an ejector device, and a piston having a cylindrical circumferential surface and disposed for movement in the longitudinal direction of the cartridge which is provided for sealing off the cartridge interior as well as for dispensing the paste material. In order to attach the cartridge securely to an ejector device and assure a high standard of hygiene, the end of the outlet tip remote from the container unit, at which an outlet orifice is disposed, is at a radial distance from the axis of the container unit that is no more than exactly as great as the radius of the container unit. The mounting is configured as a screw thread and the protective cap as a cylinder closed at one end, whose inside diameter is at least just as great as the outside diameter of the container unit, the protective cap encasing the container unit.

11 Claims, 2 Drawing Sheets

CARTRIDGE FOR CONTAINING MATERIAL IN PASTE FORM

BACKGROUND OF THE INVENTION

The invention relates to a cartridge for containing material in paste form, having a cylindrical container unit, an outlet tip with an outlet passage at one end of the container at an angle to its axis, a cap protecting the outlet nozzle, a fastening means disposed at the second end of the cylindrical container unit and provided for attaching the cartridge to an ejector device, and having a piston which has a cylindrical outer surface and is disposed for movement lengthwise of the cartridge so as to eject the paste material. The invention furthermore relates to a cap to protect a cartridge and an ejector device for manipulating the cartridge.

Such cartridges and corresponding ejectors are disclosed, for example, in U.S. Pat. No. 4,391,590. These cartridges serve for the dispensing of dental material by the dentist. A filling material for teeth, for example, is loaded into the cartridge. The cartridge is placed in an ejector device whereby the material is forced out of the cartridge with a piston, into a tooth cavity for example. For this purpose the known cartridge has a mounting flange with which it is held in the ejector device. The cartridge itself has an outlet tip which is closed with a cap. The back end of the cartridge is closed by a piston. The mounting of such a cartridge is relatively complicated, because the force required for the ejection of the dental material has to be withstood by the relatively small flange. To insert the cartridge into an ejector device, the cartridge has to be grasped by the dentist or by an assistant, with the result that germs can be transferred to its surface. Since such cartridges are held by their cylindrical barrel, any germs on the ejector device can be transferred directly onto the cartridge, and can pass from there into the patient's mouth.

SUMMARY OF THE INVENTION

The problem to which the present invention is addressed is to make available a cartridge which can be connected securely to an ejector device for dispensing the dental material while being uncontaminated or only minimally contaminated by the surface that comes in contact with the patient's mouth, and to make available an ejector device suitable therefor.

This problem is solved by the present invention in that the end of the outlet tip remote from the container, in which an outlet orifice is disposed, is at a radial distance from the axis of the container, which is precisely as great as the radius of the container (the tip is thus situated within an imaginary prolongation of the barrel of the container); in that the protective cap is configured as a cylinder closed at one end, whose inside diameter is as great as the outside diameter of the container, and in that the cap encases the container (with the exception of the cross section opening into the mounting). The inside diameter of the cap must be such that the cap will be in contact with the circumference of the container and will not come loose from it without the application of an external force. Such a cartridge can be fastened very tightly to the ejector device; a threaded connection withstands even greater forces. The container is screwed onto the ejector device by means of the cap. This signifies that, in its manipulation, the cartridge is grasped and held by the cap until it is inserted into the ejector device; the container itself does not come in contact with the dentist or the dentist's hand. The cap is on the container, that is, it is in contact with it, so that the container is not contaminated. It is desirable for an annular abutment to be formed on the cap between the container and the fastening part, and for it to abut against the open end of the cap. Thus, an especially tight seal is achieved, and with it an especially good protection of the external surface of the container.

The piston has advantageously on its cylindrical circumference at least one circumferential sealing ring and the two ends of the piston are of identical configuration. This, on the one hand, permits easy mounting of the piston inside of the container and the fastening part of the cartridge, and on the other hand it assures a good seal between the piston and the interior of the container. Preferably the ends of the piston are of truncoconical shape.

It is desirable that bosses be formed on the circumference of the container in the area of its rear end facing the fastening part, which will engage indentations in the inside surface of the cap near its open end. This embodiment results in the positive fixation of the cap on the container in addition to its frictional grip, thus improving safety when the cartridge is screwed into an ejector device, since the torque can be increased as it is screwed in. The indentations do not cover the entire inside circumference of the cap and thus they form an abutment for the bosses on the container. An inverse arrangement is also possible, that is to say, the bosses are provided on the cap and the recesses on the container.

It is desirable for the mouth at which the outlet passage joins the container to intersect the axis of the container. Thus, on the one hand a sufficiently long outlet tip is achieved, and on the other hand the amount of the residue remaining in the container is minimized.

In an additional advantageous embodiment of the invention, the inside surface of the closed end of the cap is of a conical shape, the cone being at an angle to the longitudinal axis of the cap, which is approximately equal to the angle between the axis of the container and the surface of the outlet orifice. The closed end of the cap will then make contact with the outlet orifice after it is placed on the container, so that the material in the container of the cartridge is given additional protection against the ambient atmosphere or against the entry of germs.

Especially when the cartridge is stored upright or held upright in a rack, it is advantageous to provide on the end surface of the cap an identification of the content of the container, in order to facilitate the correct selection of the cartridge from a plurality of other cartridges of different content. Also, an information medium can be disposed on the outer cylindrical surface of the cap, containing additional information on the cartridge. Such information or data can be in a variety of forms: a legend, a color code, a magnetic coding, or for example a relief-like configuration.

The problem is solved by the invention for a protective cap, in that the cap is of cylindrical shape with a closed end and an open end, the face of the closed end bearing data to identify the content of the cartridge. In particular, indentations can be disposed on the interior wall of the cap near the open end, without occupying the entire interior circumference of the cap. Instead of indentations, bosses can also be provided. The interior surface of the closed end of the cap can, as already described, have a conical shape.

The ejector device according to the invention for holding a cartridge, with a guiding tube and a plunger movably disposed in the barrel of the guiding tube, with a handle disposed at one end of the guiding tube on which a lever is provided for exercising a force acting longitudinally on the plunger, and with a mounting means disposed at the other end of the cartridge guiding tube, the mounting means having an opening (a bore, for example) running lengthwise which forms a continuation of the barrel, is characterized in that the mounting has a screw thread around the opening for engaging a complementary screw thread on the cartridge. Such an ejector device is suitable for receiving the cartridge according to the invention, and thereby it assures excellent protection of the cartridge against contamination. In particular, the mounting can have around the thread at its outside end an abutment for contact with a cap abutment of the cartridge in order on the one hand to assure a firm seating of the cartridge within the ejector device and on the other hand to define the position of the cartridge, especially the position of the outlet tip relative to the ejector device, since the cap abutment defines the depth to which the cartridge can be screwed in.

An embodiment of the invention will now be explained with the aid of a drawing, wherein:

BRIEF DESCRIPTION OF THE INVENTION

FIG. 1 is a cross section through the compule including the cap.

FIG. 2 a top view of the container of the compule.

FIG. 3 a top view of the protective cap, and

FIG. 4 an ejector device with the compule screwed on.

DETAILED DESCRIPTION OF THE INVENTION

Figure 1:
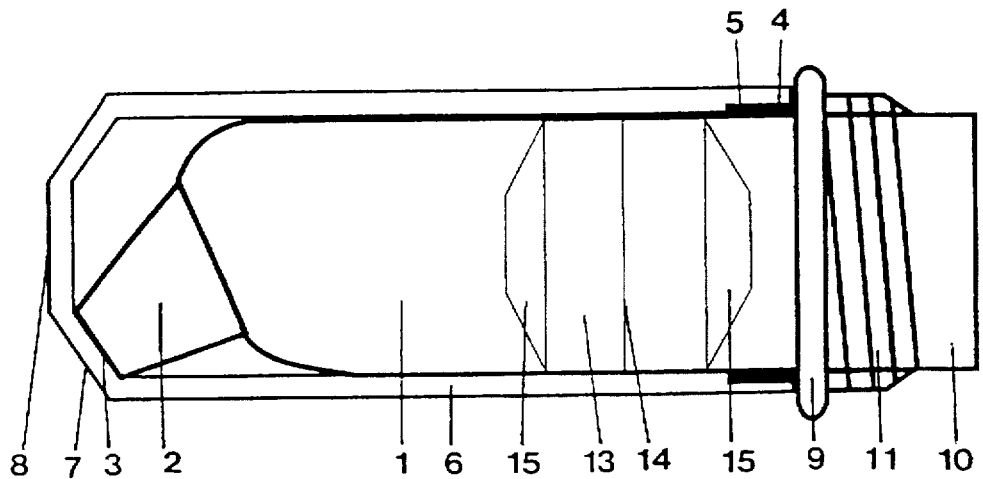
Figure 2:
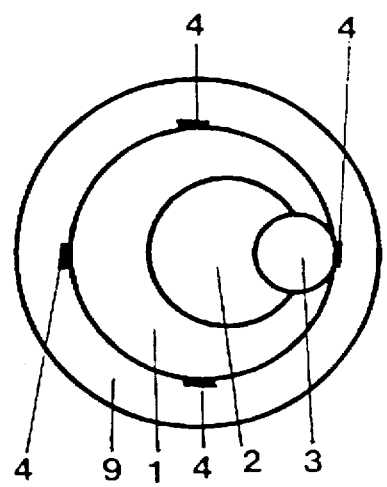
Figure 3:
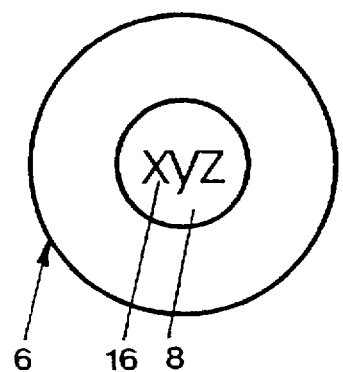
Figure 4:
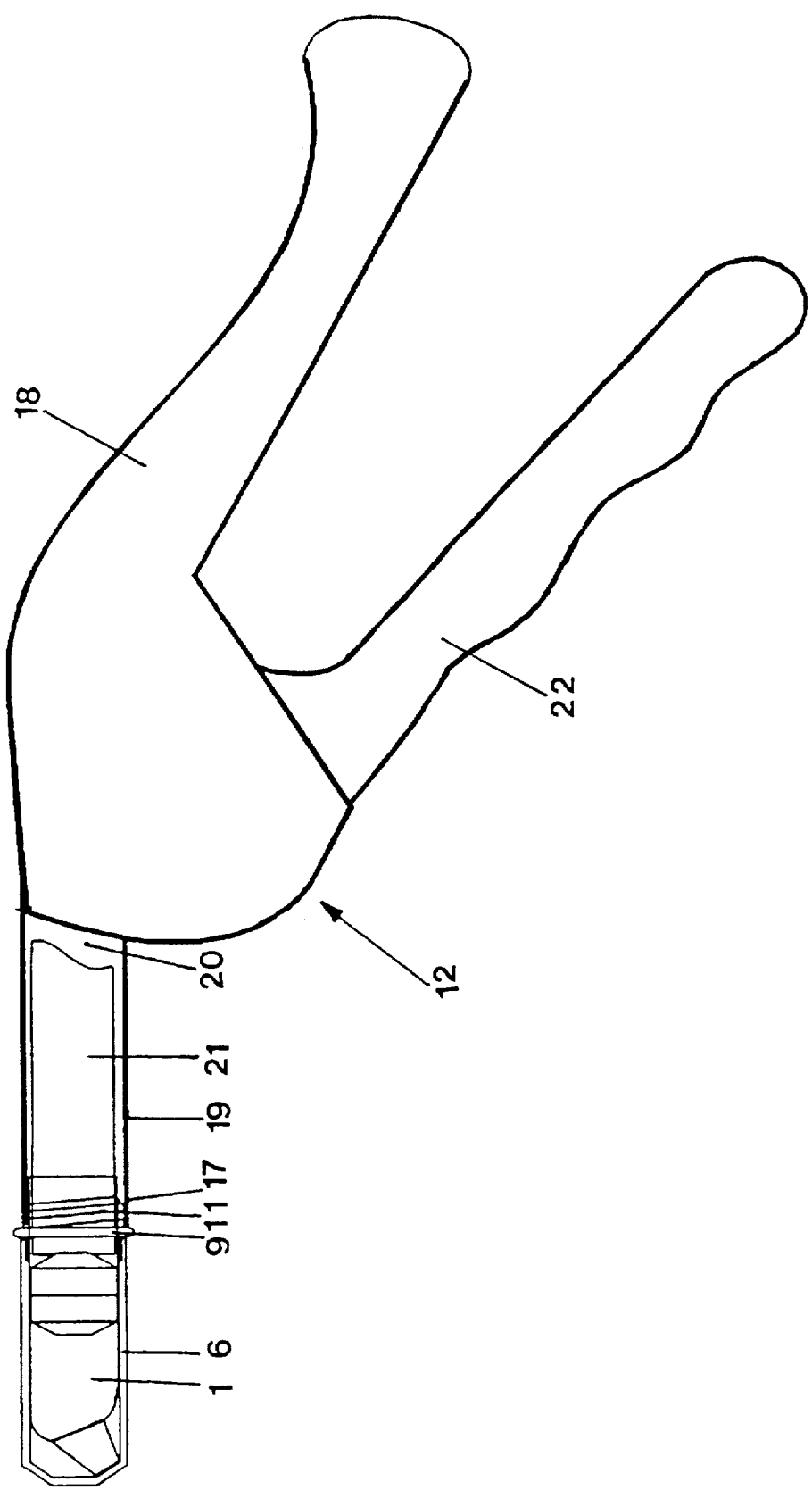

The compule has a container 1 for dental materials in paste form, such as tooth filling materials. At one end of the container 1 an outlet tip 2 is provided which has an outlet passage not seen in the drawing, which leads into an outlet orifice 3. At its other end the outlet passage opens into the container 1, intersecting the longitudinal axis of the container 1. The container 1 has at its other end the bosses 4 which engage indentations 5 in a protective cap 6 which lies against the outer cylindrical surface of the container 1 and encases the latter. The conical portion 7 of the end face 8 of the protective cap 6 is in contact with the outlet orifice 3, so that the latter is sealed. The rear, open end of the cap 6 lies against a cap abutment 9 which is formed around the circumference of the container 1 and separates the container 1 from a mounting stub 10. The mounting stub 10 has a screw thread 11 and serves for fastening the cartridge in an ejector device 12 (FIG. 4). The cartridge is closed at its open end, i.e., at the mounting stub 10, by a piston 13. The piston 13 serves on the one hand as a closure and on the other hand it serves for forcing the paste material out of the cartridge. The piston 13 has a circumferential sealing ring 14 (a plurality of sealing rings 14 can also be provided) and is configured at both its ends as a truncated cone 15. On the end face 8 of the protective cap 6 a legend 16 is marked to indicate the contents of the container 1. On the cylindrical surface of the cap 6 a data medium is placed, such as an imprint or a magnetic code. The legend 16 can be in the form of an imprint, magnetic code, or in another form such as raised print.

The cartridge is screwed with its mounting stub 10 into a socket 17 in the ejector device 12. The ejector device 12 has a hand grip 18 in which the guiding sleeve 19 is disposed. The guiding sleeve 19 has at its front end the socket 17. The guiding passage 20 of the guiding sleeve 19 leads into an opening in the socket 17 in which an internal thread is provided for receiving the thread 11 of the mounting stub 10 of the cartridge. A plunger 21 is provided for movement lengthwise within the guiding passage 20 of the ejector device 12. The plunger 21 is mechanically coupled within the hand grip 18, which is in the form of a housing, to a lever 22. This coupling can be created in any known manner. Only by way of example, reference is here made to a coupling according to U.S. Pat. No. 4,391,590, that is, the portion of the lever 22 situated within the housing of the hand grip 18 acts upon one end of the plunger 21. Any other kind of coupling permitting longitudinal movement of the plunger is possible. The ejector device 12 represented in FIG. 4 and described above permits the employment of the cartridge according to the invention and assures hygienic use of the cartridge, that is, a maximum cleanliness in the cartridge's container 1 which comes in contact with the patient, since the cartridge can be inserted into the ejector device 12 without touching the container 1. Then the cap 6 is removed. The bosses 4, which engage the recesses 5, provide for good guidance while screwing in the cartridge and for the necessary torque for the firm seating of the cartridge in the ejector, device 12. At the same time the cap abutment 9 acts on the one hand as a seal for the surface of the container 1 since the cap 6 lies against the cap abutment 9. On the other hand, the cap abutment 9 defines the depth of insertion of the cartridge into the ejector device 12, so that the outlet tip 2 will be in a predefined orientation relative to the ejector device 12. The information 16 on the end 8 of the cap 6 permits the immediate location of and access to the correct cartridge from among a plurality of cartridges arranged upright on a tray. Additional media can be placed on the cylindrical wall of the cap 6, bearing data on the date of manufacture, expiration date, etc.

What is claimed is:

1. A cartridge for containing material in paste form, comprising: a substantially cylindrical container; an outlet tip disposed on one end of the container at an angle thereto; a protective cap encasing the outlet tip; a mounting disposed on the other end of the cylindrical container configured for attaching the cartridge to an ejector device; a piston having a cylindrical circumferential external surface and sealingly mounted for movement lengthwise in the cylindrical container; wherein the outlet tip has one end remote from the container and in which an outlet orifice is disposed; wherein the one end of the outlet tip is at a radial distance from a central axis of the container and which is at most exactly as great as a radius of the container; wherein the mounting comprises a mounting stub configured as a screw thread; wherein the protective cap is configured as a cylinder closed at one end and having an inside diameter which is at least as great as an outside diameter of the container; and wherein the protective cap encases the container.

2. The cartridge according to claim 1, further comprising an annular cap abutment between the container and the mounting stub and on which the open end of the protective cap abuts.

3. The cartridge according to claim 2, further comprising bosses formed on the circumference of the container in an area of a rearward end facing the mounting stub, wherein the bosses engage indentations in an interior surface of the protective cap at the open end, wherein the indentations do not involve the entire inside circumference of the protective cap.

4. The cartridge according to claim 1, wherein the piston is cylindrical and has at least one circumferential sealing ring on the circumference, and wherein the two ends of the piston are of identical configuration.

5. The cartridge according to claim 4, wherein the ends of the piston are truncoconical in shape.

6. The cartridge according to claim 1, wherein a mouth of the outlet orifice into the container intersects the central axis of the container.

7. The cartridge according to claim 1, wherein an inside surface of the closed end of the protective cap is conical in shape and having an angle to the longitudinal axis of the protective cap that is approximately of the same size as the angle between the axis of the container and the surface of the outlet orifice, and the closed end of the protective cap lies against the outlet orifice after the container is mounted.

8. The cartridge according to claim 1, wherein an end face of the protective cap has a legend to identify the content of the container.

9. The cartridge according to claim 1, further comprising an information medium disposed on the outer cylindrical surface of the protective cap.

10. A protective cap for a cartridge having a cylindrical configuration with a closed end and an open end, wherein a face of the closed and bears information identifying the content of the cartridge and wherein an inside circumferential surface of the protective cap has indentations disposed in the area of the open end, which do not involve the entire inside circumference of the protective cap.

11. The protective cap according to claim 10, wherein the inside surface of the closed end of the protective cap is of conical shape.

* * * * *